(12) United States Patent (10) Patent No.: US 7,648,474 B2
Paolini et al. (45) Date of Patent: Jan. 19, 2010

(54) METHOD AND DEVICE FOR DETECTING THE DETACHMENT OF THE VENOUS NEEDLE FROM A PATIENT DURING DIALYSIS

(75) Inventors: Francesco Paolini, Ganaceto (IT); Carlo Alberto Lodi, Carpi (IT); Massimo Fava, Mirandola (IT)

(73) Assignee: Gambro Lundia AB (SE)

( * ) Notice: Subject to any disclaimer, the term of this patent is extended or adjusted under 35 U.S.C. 154(b) by 470 days.

(21) Appl. No.: 10/481,955

(22) PCT Filed: Jun. 24, 2002

(86) PCT No.: PCT/IB02/02354

§ 371 (c)(1), (2), (4) Date: Dec. 24, 2003

(87) PCT Pub. No.: WO03/002174

PCT Pub. Date: Jun. 9, 2003

(65) Prior Publication Data

US 2004/0171977 A1  Sep. 2, 2004

(30) Foreign Application Priority Data

Jun. 29, 2001 (IT) .................... MI2001A001395

(51) Int. Cl.
*A61M 37/00* (2006.01)
*A61M 31/00* (2006.01)
(52) U.S. Cl. ...................... 604/4.01; 604/65
(58) Field of Classification Search ....... 604/4.01–6.16, 604/65–67, 500; 73/861.18, 861.01, 861.08, 73/202.5; 210/97, 600, 633, 644–646, 736, 210/741–743, 746, 104, 141, 142; 600/300, 600/301, 322; 422/44–48
See application file for complete search history.

(56) References Cited

U.S. PATENT DOCUMENTS

| | | | | | |
|---|---|---|---|---|---|
| 4,923,598 | A | * | 5/1990 | Schal | 210/87 |
| 5,621,392 | A | * | 4/1997 | Paolini et al. | 340/603 |
| 5,657,000 | A | * | 8/1997 | Ellingboe | 340/608 |

(Continued)

FOREIGN PATENT DOCUMENTS

WO   WO 99/12588   * 3/1999

OTHER PUBLICATIONS

Kleinekofort, W., "Method to determine blood flow in vessel entrance of haemodialysis unit; involves measuring arterial and venous pressures when vessels entrance is open to allow blood flow and closed to prevent blood flow" German Patent Abstract No. DE 199 17 197 C1, Published Jul. 27, 2000.

*Primary Examiner*—Leslie R Deak
*Assistant Examiner*—Phil Wiest
(74) *Attorney, Agent, or Firm*—Finnegan, Henderson, Farabow, Garrett & Dunner L.L.P.

(57) ABSTRACT

A method of detecting the detachment of the venous needle from a patient during an extracorporeal blood treatment in a dialysis machine having an extracorporeal blood circuit provided with an arterial branch and a venous branch. The arterial pressure (Pa) is measured in the arterial branch and the venous pressure (Pv) is measured in the venous branch, and the determination is made of whether or not decreases of the arterial pressures (Pa) and venous pressures (Pv) are occurring during the dialysis treatment in normal conditions.

27 Claims, 2 Drawing Sheets

U.S. PATENT DOCUMENTS

| | | | |
|---|---|---|---|
| 5,685,989 A * | 11/1997 | Krivitski et al. | 210/646 |
| 5,720,716 A * | 2/1998 | Blakeslee et al. | 604/4.01 |
| 5,738,644 A * | 4/1998 | Holmes et al. | 604/4.01 |
| 5,910,252 A * | 6/1999 | Truitt et al. | 210/645 |
| 5,928,180 A * | 7/1999 | Krivitski et al. | 604/6.09 |
| 6,090,048 A * | 7/2000 | Hertz et al. | 600/485 |
| 6,221,040 B1 * | 4/2001 | Kleinekofort | 604/65 |
| 6,595,829 B1 * | 7/2003 | Melcer | 451/5 |
| 6,663,585 B1 * | 12/2003 | Ender | 604/6.08 |

* cited by examiner

METHOD AND DEVICE FOR DETECTING THE DETACHMENT OF THE VENOUS NEEDLE FROM A PATIENT DURING DIALYSIS

CROSS REFERENCE TO RELATED APPLICATIONS

This application is a national phase application based on PCT/IB02/02354, filed Jun. 24, 2002, the content of which is incorporated herein by reference, and claims the priority of Italian Patent Application MI2001A001395, filed Jun. 29, 2001.

BACKGROUND OF THE INVENTION

1. Field of the Invention

The present invention relates to a method of detecting the detachment of the venous needle from a patient during an extracorporeal blood treatment in a dialysis machine.

2. Description of the Related Art

As is known, blood consists of a liquid component called the blood plasma and a corpuscular component formed by the blood cells, including the red corpuscles among other components. In renal insufficiency, the blood has, in addition to the aforesaid components, particles of low molecular weight (referred to below as solute) which have to be eliminated by a dialysis treatment carried out with a dialysis machine.

A dialysis machine of the known type generally comprises an extracorporeal blood circuit, a dialysate circuit and a filter, which is located in the aforesaid circuits and comprises a blood compartment and a dialysate compartment, which are separated from each other by a semi-permeable membrane, and through which pass, respectively, the blood to be treated and the dialysate, generally flowing in counter-current mode.

During the dialysis treatment, the undesired particles contained in the blood migrate from the blood compartment to the dialysate compartment through the semi-permeable membrane both by diffusion and by convection, as a result of the passage of some of the liquid contained in the blood towards the dialysate compartment. Thus the patient will have lost some weight by the end of the dialysis process.

The extracorporeal circuit is connected to the patient by means of an arterial needle and a venous needle, which are inserted into fistulas formed in the patient's cardiovascular system, so that they can, respectively, collect the blood to be treated and return the treated blood to the patient's cardiovascular system. The extracorporeal circuit comprises a peristaltic pump and a dropper located in the arterial branch and in the venous branch respectively. The detachment of one of the aforesaid needles from the fistula causes an interruption of the access to the patient's cardiovascular system. The detachment of the venous needle, if not detected in good time, has particularly serious consequences, because it can cause a significant blood loss in the patient. Various attempts have therefore been made to provide methods for detecting the detachment of the aforesaid needles, and particularly of the venous needle.

One of the aforesaid known methods is described in WO 99/12588. This method is based on the electrical conductivity of the blood, and consists of the injection of a current into a closed circuit consisting of the extracorporeal circuit and the patient's cardiovascular system, and the measurement, by means of a measuring instrument located in the aforesaid extracorporeal circuit, the current variations which are caused by the detachment of one or both of the needles. For this method, the current injection and the measurement of the current variation have to be carried out by inductive coupling, in other words by means of windings located at specified points along the extracorporeal blood circuit.

The method described above has various drawbacks. In particular, this method, although theoretically valid, cannot provide satisfactory results from the practical point of view, since the high electrical impedance produced by the peristaltic pump, which effectively interrupts the continuity of the blood flow, makes it necessary to operate with relatively high currents in order to make use of the low conductivity of the materials, generally PVC, which are used to form the extracorporeal circuit, the filter, the peristaltic pump and the dropper. The use of relatively high currents is most inadvisable in a machine connected to a patient, and, even if these currents could be used, it would not be possible to transmit them by means of an inductive coupling, which, among other considerations, generates additional parasitic currents which interfere with measurements. In some dialysis machines, the dropper also creates a high impedance, of the same order of magnitude as that created by the peristaltic pump, and thus exacerbates one of the problems described above.

Consequently, because there is a requirement to operate with relatively low currents, and because the impedance of the peristaltic pump, and of the dropper in most cases, is high, the detachment of one of the needles causes current variations which are not easily identifiable and which can be confused with the background noise of the measuring instrument.

Furthermore, this method does not allow for the fact that the patient may be connected to earth and that the filter itself is necessarily connected to earth, since the dialysate circuit is connected to earth to meet the requirements of the safety regulations for dialysis machines. Therefore the electrical circuit assumed in the aforesaid application does not truly represent the real analogy of a dialysis machine in electrical terms.

It is also known from U.S. Pat. No. 6,221,040 a method for monitoring vascular access using pressure signals in a way different from the present invention.

The object of the present invention is to provide a method of detecting the detachment of the venous needle from a patient during an extracorporeal blood treatment in a dialysis machine, which overcomes the drawbacks of the known art.

SUMMARY OF THE INVENTION

According to the present invention, a method is provided for detecting the detachment of the venous needle from a patient during an extracorporeal blood treatment in a dialysis machine having an extracorporeal blood circuit comprising an arterial branch and a venous branch, the method comprising the steps of measuring the arterial pressure in the arterial branch and the venous pressure in the venous branch, and determining whether or not essentially simultaneous decreases of the arterial and venous pressures are occurring during the dialysis treatment in normal conditions.

The present invention also relates to a device for detecting the detachment of the venous needle from a patient during an extracorporeal blood treatment in a dialysis machine.

According to the present invention, a device is provided for detecting the detachment of the venous needle from a patient during an extracorporeal blood treatment in a dialysis machine having an extracorporeal blood circuit comprising an arterial branch and a venous branch, the device being characterized in that it comprises pressure detectors for measuring the arterial pressure in the arterial branch and the venous pressure in the venous branch, and a control unit for determining whether or not decreases of the arterial and venous pressures are occurring during the dialysis treatment in normal conditions.

Note that the control unit evaluates preferably if said decreases of the venous and arterial pressures are occurring in a time interval, which is relatively short (some seconds).

BRIEF DESCRIPTION OF THE DRAWINGS

To enable the present invention to be more clearly understood, a preferred embodiment of it will now be described, purely by way of example and without restrictive intent, with reference to the attached figures, of which

DETAILED DESCRIPTION OF THE INVENTION

Figure 1:
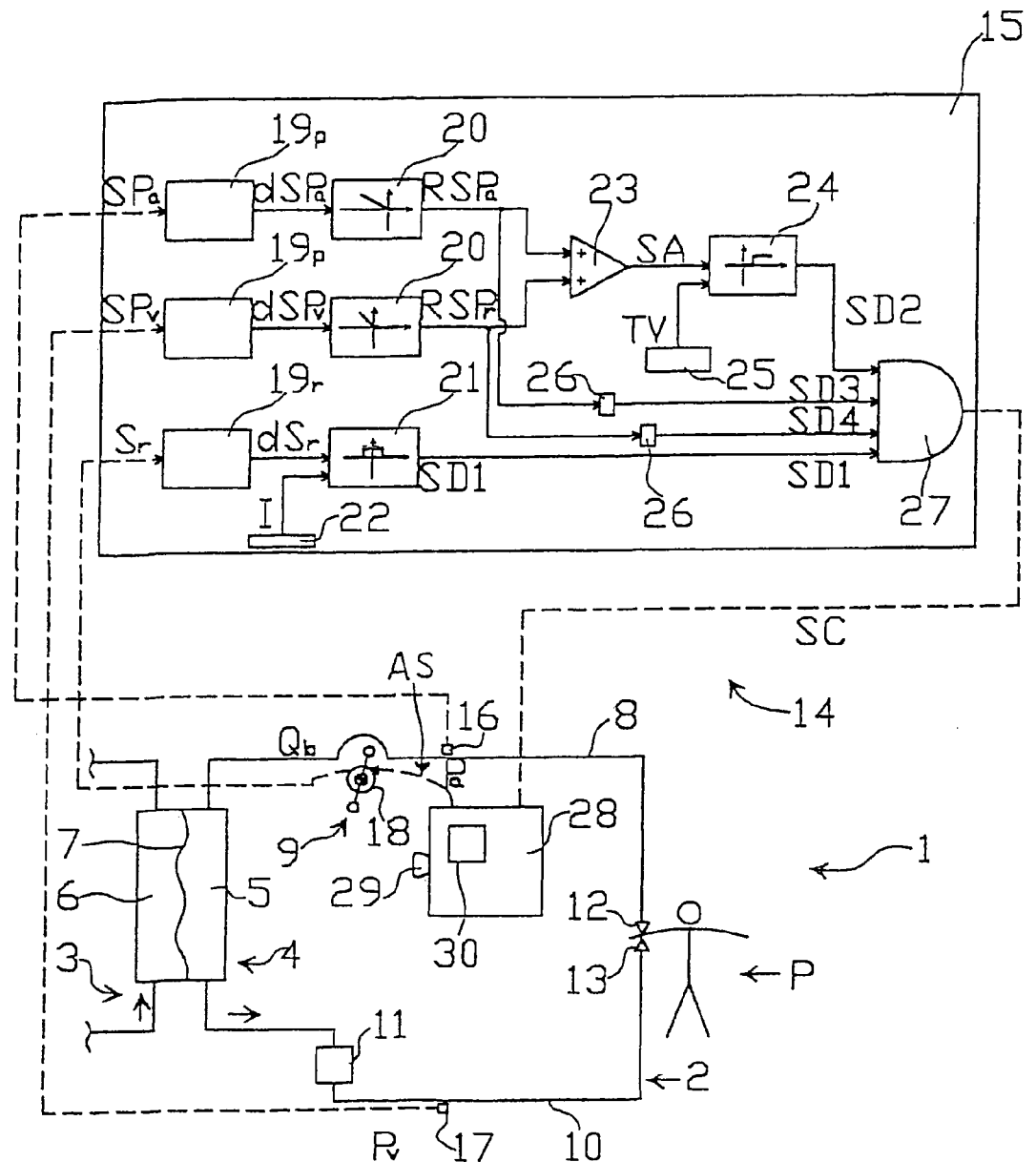
FIG. 1 is a schematic view, with parts removed for clarity, of a dialysis machine fitted with a device for detecting the detachment of the venous needle, constructed according to the present invention.

In FIG. 1, the number 1 indicates the whole of a dialysis machine connected to a patient P. The machine 1 comprises an extracorporeal blood circuit 2, a dialysate circuit 3 and a filter 4, which comprises a blood compartment 5 and a dialysate compartment 6 separated by a semi-permeable membrane 7.

The extracorporeal blood circuit 2 comprises an arterial branch 8, in which is located a peristaltic pump 9 providing a flow Qb of blood, and a venous branch 10, in which is located a dropper 11. The arterial branch 8 has one end connected to the blood compartment 5 and one end provided with an arterial needle 12, which, when in use, is inserted into a fistula (not shown) in the patient P to collect the blood from the cardiovascular system of the patient P, while the branch 10 has one end connected to the blood compartment 5 and an opposite end provided with a venous needle 13, which, when in use, is inserted into the aforesaid fistula (not shown) to return the treated blood to the cardiovascular system of the patient P. The branches 8 and 10 are tubes made from plastic material, generally PVC, and are used, respectively, to supply the blood to be treated to the compartment 5 and to introduce the treated blood leaving the compartment 5 into the cardiovascular system. The filter 4 and the dropper 11 are also, made from plastic material, generally PVC.

The machine 1 also comprises a device 14 for detecting the detachment of the venous needle 13. The operation of the device 14 is based on experimental measurements carried out by the applicant. The graphs in FIGS. 2 to 4 relate to experimental measurements made by the applicant and show a transitory time interval _t1 in which the blood flow Qb is, made to vary; two time intervals _t2 and _t3 in which the blood flow Qb is kept essentially constant; and a time interval _ t4 in which the blood flow is reduced to zero, or in other words the dialysis treatment is interrupted. The measurements which were made indicated that, during dialysis treatment in standard conditions, in other words with a constant blood flow Qb, the variations of the arterial pressure Pa and venous pressure Pv found in the arterial branch 8 and in the venous branch 10 respectively are essentially of opposite sign. In other words, a decrease in arterial pressure Pa in the arterial branch 8 generally corresponds to an increase in the pressure Pv in the venous branch 10, and vice versa. The applicant has found that, when the venous needle 13 is detached in the interval _t3, both the arterial pressure Pa in the arterial branch 8 and the venous pressure Pv in the venous branch 10 decrease significantly when the blood flow Qb is constant.

In order to determine the variations of arterial pressure Pa and venous pressure Pv indicating the detachment of the venous needle 13, the device 14 comprises a control unit 15, a pressure detector 16 located in the arterial branch 8 up-line from the peristaltic pump 9, a pressure detector 17 located in the venous branch 10 near the dropper 11, and an encoder 18 for measuring the speed of revolution of the rotor of the peristaltic pump 9. The control unit 15 receives a signal Sr from the encoder 18, correlated with the speed of revolution of the rotor of the peristaltic pump 9, and two signals Spa and SPv, correlated with the arterial pressure Pa and venous pressure Pv, from the two detectors 16 and 17 respectively.

The unit 15 can process the signals Sr, Spa and SPv, and comprises three derivation units 19$p$ and 19$r$, which derive the signals Spa, SPv and Sr with respect to time and supply corresponding signals dSpa, dSPv and dSr, two rectification units 20 for rectifying the derived signals dSPa and dSPv and for supplying two signals RSPa and RSPv, a comparison unit 21, which receives the signal dSR and compares it with an interval I of acceptability stored in a store 22 and emits a digital signal SD1 at the output as a function of the comparison with the interval I of acceptability. The unit 15 comprises an adder unit 23, which adds the rectified signals RSPa and RSPv, and emits a signal SA equal to the sum of the rectified signals RSPa and RSPv, a comparison unit 24, which receives the output signal SA from the adder unit 23, compares the signal SA with a threshold value TV contained in a store 25, and emits a digital signal SD2. The unit 15 also comprises two conversion units 26 for converting the signals RSPa and RSPv into digital signals SD3 and SD4 respectively, and a logical operator unit 27 which receives the digital signals SD1, SD2, SD3 and SD4, compares them with a truth table, and emits a control signal SC.

The dialysis machine 1 comprises a control unit 28, which is connected to the control unit 15 of the device 14 for receiving the control signal SC, and is also connected to the peristaltic pump 9. The unit 28 comprises an acoustic warning device 29 and a visual indicator 30 to alert the operator and user to the detachment of the venous needle 13.

Figure 2:
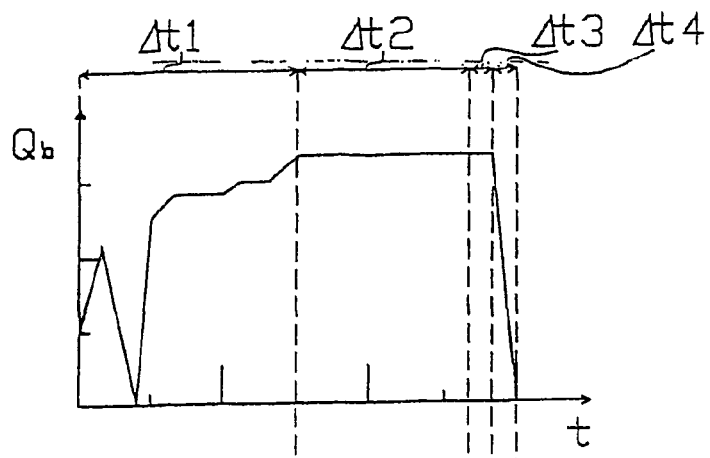
FIG. 2 is a graph showing the blood flow, recorded in the extracorporeal blood circuit in a dialysis machine during an experimental test which simulates a dialysis treatment with detachment of the venous needle.

In use, the dialysis machine 1 is connected to a patient P as shown schematically in FIG. 1. During a dialysis treatment in standard conditions, the blood flow Qb is kept essentially constant as shown in the graph of FIG. 2 in the intervals _t2 and _t3. In FIG. 2, the blood flow Qb varies in an initial time interval _t1, and is then kept constant in successive time intervals _t2 and _t3, until it is brought to zero in the interval _t4 following the detachment of the venous needle 13.

Figure 3:
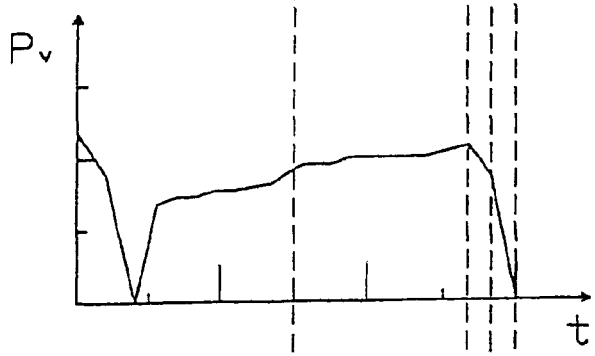
FIGS. 3 and 4 are graphs showing the venous pressure and arterial pressure measured in the extracorporeal blood circuit of the dialysis machine during the experimental tests to which the graph of FIG. 2 relates.
Figure 4:
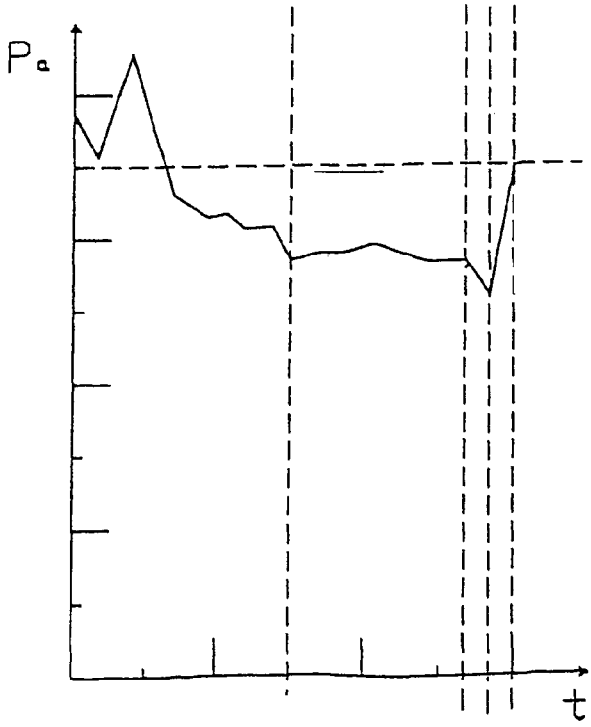

The graphs of FIGS. 3 and 4, which have a time scale identical to the time scale, of the graph of FIG. 2, show the generally differing trends of the variations of the venous pressure Pv and arterial pressure Pa with a constant flow Qb in the time interval _t2, and the uniform decrease in the venous pressure Pv and arterial pressure Pa in the time interval _t3, during which the venous needle 13 has become detached and the peristaltic pump 9 has not yet been stopped. The peristaltic pump 9 is then stopped and the dialysis treatment is interrupted to prevent loss of blood from the patient P.

With reference to FIG. 1, during the dialysis treatment the speed of revolution of the peristaltic pump 9 and the arterial pressure Pa and venous pressure Pv are constantly measured by the encoder 18 and by the detectors 16 and 17. The speed of revolution of the rotor of the peristaltic pump 9 is correlated with the flow Qb, and this measurement is equivalent for practical purposes to a measurement of the flow Qb, once the characteristics of the pump 9 and the dynamic conditions of the extracorporeal circuit 2 are known. The pressure signals SPa and SPb undergo derivation in the corresponding derivation units 19p, and the derived signals dSPa and dSPv are rectified in the corresponding rectification units 20. In the rectification unit 20, each of the signals RSPa and RSPv takes a value of zero when the corresponding input signal dSPa or dSPv is positive (increasing pressure) and takes a positive value, proportional to the input signal dSPa or dSPv, when the corresponding input signal dSPa or dSPv is negative (falling pressure). The derived signal dSr is compared with the interval I of acceptability in the comparison unit 21, which supplies a digital signal SD1 which is equal to one when the derived signal dSr falls within the acceptability interval (constant flow Qb) and is equal to zero when the derived signal dSr falls outside the acceptability interval (variable flow Qb). In practice, the signal SD1 is equal to one when the flow Qb is essentially constant, and equal to zero when the flow Qb is significantly varied.

The adder unit 23 adds the rectified signals RSPa and RSPv and compares the sum SA with the threshold value TV, and supplies a digital signal SD2 which is equal to one when the sum SA is greater than the threshold value TV, and a digital signal SD2 which is equal to zero when the sum SA is smaller than the threshold value TV.

The values of the digital signals SD3 and SD4 are equal to one when the corresponding rectified signals RSPa and RSPv are greater than zero, and equal to zero when the corresponding rectified signals RSPa and RSPv are equal to zero.

The logical operator unit 27 receives the signals SD1, SD2, SD3 and SD4 and compares these signals with a truth table, and supplies at its output a digital signal SC which is equal to one when all the signals SD1, SD2, SD3 and SD4 are equal to one, while the signal SC takes a value equal to zero when only one of the signals SD1, SD2, SD3 and SD4 is equal to zero. From the practical point of view, with reference to FIGS. 2 to 4 and to the time interval _t2, the flow Qb is constant and the signal SD1 is equal to one, the rectified signals SD3 and SD4 will both be equal to zero or at least one will be equal to zero. Because of the slight variations of the pressures Pa and Pv in the interval _t2, the sum SA is less than the threshold value TV, which is selected experimentally to discriminate negligible variations of the arterial pressures Pa and venous pressures Pv from significant variations. Consequently, the signal SC is equal to zero.

With reference to the interval _t3, the abrupt decrease of the arterial pressures Pa and venous pressures Pv causes both the signals RSPa and RSPv to be positive and their sum SA to be greater than the threshold value TV. This causes SD2, SD3 and SD4 to be equal to one. The constancy of the flow Qb also causes the signal SD1 to be equal to one, and therefore the signal SC will also be equal to one, which is the value that indicates that the venous needle has become detached.

The signal SD2 provides a measurement of the degree of the decrease of the arterial pressures Pa and venous pressures Pv and the threshold value TV makes it possible to discriminate the very slight decreases in the aforesaid pressures, which may occur from time to time even without the detachment of the venous needle, from the significant decreases which occur when the venous needle 13 actually becomes detached.

The signal SC is transmitted to the unit 28, which emits an alarm signal AS to stop the peristaltic pump 9 and the dialysis treatment when SC is equal to one.

As an alternative to the stopping of the peristaltic pump 9, or in addition to it, the alarm signal AS can trigger the activation of the acoustic warning device 29 and/or the visual indicator 30.

The invention claimed is:

1. A method of detecting the detachment of a venous needle from a patient during an extracorporeal blood treatment in a dialysis machine having an extracorporeal blood circuit comprising an arterial branch and a venous branch, the method comprising the steps of:
    measuring an arterial pressure in the arterial branch and a venous pressure in the venous branch;
    determining whether or not decreases of the arterial pressures and venous pressures are occurring during the dialysis treatment in normal conditions;
    measuring a blood flow along the extracorporeal blood circuit;
    determining whether the blood flow is essentially constant during a time interval in which said decreases of arterial pressure and venous pressure have occurred; and
    emitting an alarm signal when all of the following conditions are present during said time interval:
        a decrease in the arterial pressure;
        a decrease in the venous pressure; and
        the blood flow along the extracorporeal blood circuit is essentially constant.

2. The method according to claim 1, wherein the value of said decreases of arterial pressure and venous pressure is evaluated.

3. The method according to claim 2, wherein a signal correlated with the sum of the decreases of arterial pressure and venous pressure is compared with an experimentally determined threshold value.

4. The method according to claim 3, wherein an alarm signal is emitted when the additional following condition is present during said time interval:
    the signal correlated with the sum of the decreases of arterial pressure and venous pressure is greater than said threshold value.

5. The method according to claim 4, wherein said blood flow is stopped in said extracorporeal circuit by means of said alarm signal, to interrupt the dialysis treatment.

6. The method according to claim 4, wherein an acoustic warning device is activated by means of said alarm signal.

7. The method according to claim 4, wherein a visual indicator is activated by means of said alarm signal.

8. The method according to claim 1, wherein measuring a blood flow along the extracorporeal blood circuit comprises measuring a speed of a pump providing said blood flow.

9. The method according to claim 8, wherein the pump providing said blood flow is a peristaltic pump located in said arterial branch.

10. The method according to claim 8, wherein measuring a speed of a pump comprises measuring a speed of revolution of a rotor of the pump.

11. A device for detecting the detachment of a venous needle from a patient during an extracorporeal blood treatment in a dialysis machine having an extracorporeal blood circuit comprising an arterial branch and a venous branch, the device comprising:
    pressure detectors for measuring an arterial pressure in the arterial branch and a venous pressure in the venous branch;

means for measuring a blood flow along the extracorporeal blood circuit; and a control unit comprising:
  means for determining whether or not decreases of arterial pressure and venous pressure are occurring during the dialysis treatment in normal conditions;
  means for determining whether the blood flow is essentially constant during a time interval in which said decreases of arterial pressure and venous pressure have occurred; and
  means for emitting an alarm signal when all of the following conditions are present during said time interval:
    a decrease in the arterial pressure;
    a decrease in the venous pressure; and
    the blood flow along the extracorporeal blood circuit is essentially constant.

12. The device according to claim 11, wherein said emitting means comprise means for emitting an alarm signal when the additional following condition is present during said time interval:
  a signal correlated with the sum of the decreases of arterial pressure and venous pressure is greater than a threshold value.

13. The device according to claim 11, wherein said determining means comprise a derivation unit for emitting a signal correlated with the derivative of the blood flow and a first comparison unit for determining whether the signal correlated with the derivative of the blood flow falls within an interval of acceptability.

14. The device according to claim 11, wherein said control unit comprises means for discriminating the value of the decreases of the arterial pressure and venous pressure.

15. The device according to claim 13, wherein said control unit comprises a logical operator unit which can emit a control signal as a function of the decreases of arterial pressure and venous pressure, and an output signal from the first comparison unit.

16. The device according to claim 11, wherein said means for measuring a blood flow comprise means for measuring a speed of a pump providing said blood flow.

17. The device according to claim 16, wherein the pump providing said blood flow is a peristaltic pump located in said arterial branch.

18. The device according to claim 16, wherein the means for measuring a speed of a pump comprise an encoder for measuring a speed of revolution of a rotor of the pump.

19. A dialysis machine comprising:
  an extracorporeal blood circuit comprising an arterial branch and a venous branch; and
  a device for detecting the detachment of a venous needle from a patient during an extracorporeal blood treatment, the device comprising:
  pressure detectors for measuring an arterial pressure in the arterial branch and a venous pressure in the venous branch;
  means for measuring a blood flow along the extracorporeal blood circuit; and
  a control unit comprising:
    means for determining whether or not decreases of arterial pressures and venous pressures are occurring during the dialysis treatment in normal conditions;
    means for determining whether the blood flow is essentially constant during a time interval in which said decreases of arterial pressure and venous pressure have occurred; and
    means for emitting an alarm signal when all of the following conditions are present during said time interval:
      a decrease in the arterial pressure;
      a decrease in the venous pressure; and
      the blood flow along the extracorporeal blood circuit is essentially constant.

20. The dialysis machine according to claim 19, further comprising a peristaltic pump located in said arterial branch, and a dropper located in said venous branch.

21. The dialysis machine according to claim 20, wherein said pressure detectors comprise a first detector located in the arterial branch up-line from the peristaltic pump, and a second detector located in the venous branch near the dropper.

22. The dialysis machine according to claim 19, further comprising an additional control unit comprising means for receiving a control signal from said control unit and emitting an alarm signal as a function of the control signal, said additional control unit comprising a warning device which can be activated by means of said alarm signal.

23. The dialysis machine according to claim 19, further comprising an additional control unit which can receive a control signal from said control unit and emit an alarm signal as a function of the control signal, said additional control unit comprising a visual indicator which can be activated by means of said alarm signal.

24. The dialysis machine according to claim 19, further comprising an additional control unit comprising means for receiving a control signal from said control unit and emitting an alarm signal as a function of the control signal, said alarm signal being emitted when all the following conditions are present during said time interval:
  a decrease in arterial pressure;
  a decrease in venous pressure;
  a signal correlated with the sum of the decreases of arterial pressure and venous pressure is greater than a threshold value; and
  the blood flow is essentially constant.

25. The dialysis machine according to claim 19, wherein the means for measuring a blood flow along the extracorporeal blood circuit comprise means for measuring a speed of a pump providing said blood flow.

26. The dialysis machine according to claim 25, wherein the pump providing said blood flow is a peristaltic pump located in said arterial branch.

27. The dialysis machine according to claim 25, wherein the means for measuring a speed of a pump comprise an encoder for measuring a speed of revolution of a rotor of the pump.

* * * * *

UNITED STATES PATENT AND TRADEMARK OFFICE
CERTIFICATE OF CORRECTION

PATENT NO.      : 7,648,474 B2                          Page 1 of 1
APPLICATION NO. : 10/481955
DATED           : January 19, 2010
INVENTOR(S)     : Francesco Paolini et al.

It is certified that error appears in the above-identified patent and that said Letters Patent is hereby corrected as shown below:

On the Title page, item (87), "PCT Pub. Date: Jun. 9, 2003" should read --PCT Pub. Date: Jan. 9, 2003--.

Signed and Sealed this

Ninth Day of March, 2010

David J. Kappos
*Director of the United States Patent and Trademark Office*